United States Patent [19]

Lai

[11] 4,167,512

[45] Sep. 11, 1979

[54] SYNTHESIS OF 2-KETO-1,4-DIAZACYCLOALKANES

[75] Inventor: John T. Lai, Broadview Heights, Ohio

[73] Assignee: The B. F. Goodrich Company, Akron, Ohio

[21] Appl. No.: 916,640

[22] Filed: Jun. 19, 1978

Related U.S. Application Data

[63] Continuation-in-part of Ser. No. 835,066, Sep. 21, 1977, abandoned.

[51] Int. Cl.$^2$ ............................................. C07D 243/08
[52] U.S. Cl. ............................. 260/239.3 R; 544/344; 544/354; 544/384; 260/239.3 T; 260/239.3 B
[58] Field of Search ...................... 544/384, 344, 354; 260/239.3 R, 239.3 T, 239.3 B

[56] References Cited

U.S. PATENT DOCUMENTS

| | | | |
|---|---|---|---|
| 2,920,077 | 1/1960 | Bindler et al. | 544/354 |
| 4,069,195 | 1/1978 | Layer et al. | 260/45.8 NW |
| 4,073,770 | 2/1978 | Son et al. | 260/45.8 NW |

Primary Examiner—Jose Tovar
Attorney, Agent, or Firm—Alfred D. Lobo; J. Hughes Powell, Jr.

[57] ABSTRACT

Several novel syntheses have been discovered for preparation of 2-keto-1,4-diazacycloalkanes and their derivatives. Trans isomers of polysubstituted quinoxalin-2-ones may now be prepared.

3 Claims, No Drawings

SYNTHESIS OF 2-KETO-1,4-DIAZACYCLOALKANES

CROSS-REFERENCE TO RELATED APPLICATION

This application is a continuation-in-part application of Ser. No. 835,066 filed Sept. 21, 1977, now abandoned.

BACKGROUND OF THE INVENTION

Organic materials, whether natural or synthetic, are conventionally protected against degradation by ultraviolet (UV) light by incorporating a UV light stabilizer in the material. Many classes of compounds are known to be useful UV light stabilizers, some being more effective than others. Particularly effective compounds, which provide compositions resistant to degradtion by UV light, include the decahydroquinolines disclosed in copending U.S. patent applications Ser. Nos. 697,345 and 697,387, now issued as U.S. Pat. Nos. 4,073,770 and 4,069,195 respectively; the 1,5-diazacycloalkanes and 2-keto-1,5-diazacycloalkanes disclosed in copending U.S. patent Ser. No. 835,069; and, the 2-keto-1,4-diazacycloalkanes disclosed in co-pending U.S. patent application Ser. No. 835,065. Other cycloalkanes useful as UV light stabilizers are disclosed in Ger. Offen. No. 2,315,042; Japanese Pat. Nos. 7,453,571 and 7,453,572; and in U.S. Pat. Nos. 3,919,234, 3,920,659 and 3,928,330 which teach substituted piperazinediones.

The substituted piperazinediones are difficult to prepare, particularly with dialkyl substituents on each of two $N^4$-adjacent symmetrical carbon atoms (hereafter "symmetrical C atoms"). Once prepared, however, they may be reduced to the tetraalkyl substituted piperazine as disclosed in U.S. patent application Ser. No. 239,350 (Ger. Offen. No. 2,315,042). There is no suggestion as to how a mono-keto structure, that is a 2-keto-1,4-diazacycloalkane structure, may be prepared with a total of two or more (hence "polysubstituted") substituents on symmetrical C atoms.

It is known that 4,4,6,6-tetramethyl-1,5-diazacycloheptan-2-one may be prepared by a Schmidt's rearrangement of a six-membered ring with sodium azide (see German Pat. No. 2,428,877) but there is no known manner of similarly arriving at a six membered 1,4-diaza ring with an $N^1$-adjacent carbonyl.

It is known 1,4-diaza(3,3,5,5)-dipentamethylene-2-one may be prepared, starting with cyclohexanone by cyclization of bis (1-cyanocyclohexyl) amine, reducing with lithium aluminum hydride to form 1,4-diaza(2,2,5,5)-dipentamethylene-2-imino, treating with acetic anhydride and heating with hydrochloric acid. This procedure is set out in greater detail in an article by Helmut Egg in Monatshefte fur Chemie 106, 1167–1173 (1975). However, starting with acetone instead of cyclohexanone, the reactions do not proceed in an analogous manner to give 3,3,5,5-tetramethyl-piperazin-2-one. This Egg reference teaches substituted piperazines wherein each symmetrical $N^4$-adjacent carbon is part of a six membered ring and the cyclic substituent on each $N^4$-adjacent carbon is always the same. A single cyclic substituent on the $N^4$-adjacent C atom of the fixed two-carbon bridge cannot be prepared by following the techniques of Egg.

Cis-3,3-dimethyl-decahydroquinoxalin-2-one has been prepared from cis-1,2-diaminocyclohexane, and it is disclosed that the cis-compounds are valuable intermediates for the production of pharmaceuticals, textile auxiliary products and synthetic materials. This reference states that the trans-1,2-diaminocyclohexane is converted, with excess chloracetic acid, or with salts thereof, into 1,2-diaminocyclohexane-N,N'-tetraacetic acid, which is quite unlike the behavior of the cis starting material. The cis-2-keto-1,4-diazacycloalkane is prepared by reacting an aqueous solution of cis-1,2-diaminocyclohexane with acetone cyanohydrin, and heating the reaction solution to dryness. The reference does not teach formation of a trans-5,6-polyalkylene-2-keto-diazacycloalkane, and there is no suggestion as to how it could be made. In fact, it is to be understood that the trans-2-keto-1,4-diazacycloalkane cannot be made, since Bindler states that cis-1,2-diaminocyclohexane behaves differently from trans-1,2-diaminocyclohexane; the positioning of the two primary amine moieties imparts distinctly different properties to the isomers. This difference, and particularly the essential difference in cyclization behavior of the primary amine moieties, is used to advantage in the separation of the isomers. The cis isomer cyclizes and complexes with Ni and Cu; the trans isomer does not. Nevertheless we have found that trans-2-keto-1,4-diazacyclohexane can now be formed in a manner analogous to that in which the cis-2-keto-1,4-diazacyclohexane is formed.

Following the teachings of Bindler, ethylene diamine may be substituted for cyclohexanediamine, and 3,3-dimethyl-2-keto-piperazine is obtained. However, when a substituted ethylene diamine is used, the substituents appear on the No. 6 carbon of the diaza ring. For example with 1,2-propane diamine, 3,3,6-trimethyl-2-keto-piperazine is formed; and with 2-methyl-1,2-propane diamine the compound obtained is 3,3,6,6-tetramethyl-2-keto-piperazine. No. 6-substituted and 3-substituted carbons are not symmetrical carbon atoms about the same N-adjacent atom in the diaza ring (hereinafter referred to as "symmetrical N-adjacent C atoms"). These compounds are quite unlike the novel compounds claimed. Moreover, 3,3,6,6-tetraalkyl substituted diazacycloalkan-2-ones, in which the substituents are not on symmetrical N-adjacent C atoms, are relatively ineffective UV stabilizers, confirming my experience that the more substituents on symmetrical N-adjacent C atoms, the better the stabilization effect.

It is known that 2,2,4-trimethyl-tetrahydroquinoline can be hydrogenated to form a mixture of cis and trans 2,2,4-trimethyldecahydroquinoline, and, in general, the trans isomer is the major constituent. However, 2,2-dimethyltetrahydroquinoxaline is not hydrogenated in an analogous manner.

It is to the problem of synthesizing polysubstituted 2-keto-1,4-diazacycloalkanes, efficiently and economically, so that they can be manufactured for commercial use, that this invention is directed.

SUMMARY OF THE INVENTION

It has been discovered that polysubstituted 2-keto-1,4-diazacycloalkanes may be prepared from readily available starting materials, in simple, conventional apparatus, without the high risks attendant upon using hydrogen cyanide. This may be done by any of several novel syntheses.

A. A novel synthesis has been discovered wherein a cis-3,3-dialkyl-3,4-dihydroquinoxalin-2-one is hydrogenated in the presence of a suitable hydrogenation catalyst, at elevated temperature and pressure, to yield a cis-3,3-dialkyl decahydroquinoxalin-2-one.

B. A novel synthesis has been discovered wherein trans-1,2-diaminocyclohexane is reacted with acetone cyanohydrin in the presence of water to yield trans-3,3-dimethyl-decahydroquinoxalin-2-one.

C. A novel synthesis has been discovered (hereinafter referred to as "the cyanohydrin synthesis"), wherein a cyclic or acyclic 1,2-diamine is reacted with cyclic or acyclic cyanohydrins in the presence of a suitable organic solvent in the presence of aqueous NaOH at ambient temperature and pressure, in the presence of an "onium salt" (defined hereinafter) catalyst in conjunction with a haloform, to yield a polysubstituted 2-keto-1,4-diazacycloalkane.

D. A novel synthesis has been discovered (hereinafter referred to as "the ketoform synthesis") wherein a preselected 1,2-diamine is reacted with a saturated acyclic or cyclic monoketone, and, a haloform, in the presence of (i) an onium salt catalyst (ii) an organic solvent, and (iii) aqueous alkali.

DETAILED DESCRIPTION OF PREFERRED EMBODIMENTS

The basic structure of the compounds prepared by the syntheses described herein, is a polysubstituted (hereafter also referred to as "substituted" for brevity) 2-keto-1,4-diazacycloalkane having (a) a fixed two-carbon bridge between the two N atoms (the $N^1$ and $N^4$ atoms) of the diaza ring, the remaining portion of the ring having a variable length bridge of two or more carbon atoms, (b) an $N^1$-adjacent carbonyl in the fixed two-carbon bridge, and (c) at least the $N^4$-adjacent carbon of the fixed two-carbon bridge has two substituents (hence "polysubstituted"), which may be cyclizable, that is, form a cyclic substituent. These compounds which may be monocyclic, or with cyclizable substituents, may be bicyclic or tricyclic, are particularly useful as UV light stabilizers in substantially colorless organic materials. The compounds may also form dimers and bis-compounds. The diaza ring of the basic structure may have from 6 to 9 ring members, more particularly from 6 to 8 ring members, and most preferably from 6 to 7 ring members.

These substituted 2-keto-1,4-diazacycloalkanes characteristically have two substituents, which may be cyclizable, on the $N^4$-adjacent C atom of the fixed two-carbon bridge. They are particularly useful as UV light stabilizers in compositions subjected to UV light degradation. As stabilizers they are used in the range from about 0.01 to about 5 parts by weight, and preferably from about 0.1 to about 1.0 part per one hundred parts (phr) of organic material subject to UV light. These materials may be low or high molecular weight materials, and particularly include homopolymers, copolymers and mixtures thereof. Examples of materials that can be stabilized against degradation due to UV light are oils; monomers, particularly α,β-olefinically unsaturated monomers such as acrylates, dienes, vinyl nitriles, and the like; and other relatively lower molecular weight materials than synthetic resinous polymers, such as alcohols, aldehydes, and the like. Examples of known materials which can be stabilized with polysubstituted 2-keto-1,4-diazacycloalkanes are natural rubber, synthetic rubbers such as cis-polyisoprene, styrene-butadiene rubber, dienenitrile rubbers, polyepihalohydrin polymers, polyurethanes, PVC resins, ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethyl-vinyl acetate polymers, and the like. The substituted 2-keto-1,4-diazacycloalkanes can also be used to stabilize mixtures and blends of polymeric materials such as ABS resin blends, PVC and polymethacrylate blends, and blends of polyolefin homopolymers and copolymers such as blends of polypropylene in epdm polymers.

The 2-keto-1,4-diazacycloalkanes prepared by the syntheses of this invention have the structural formula:

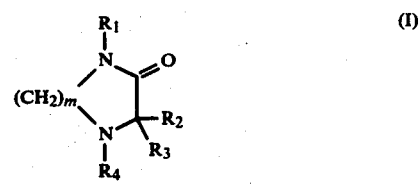

wherein, m represents an integer in the range from 2 to 7, being the number of methylene groups forming a bridge of variable length, and some of which groups (a) together with the carbons to which they are bound, may form a cyclopentyl, cyclohexyl or cycloheptyl endo ring, or (b) be substituted; when m is 2 then (I) represents a substituted 2-keto-piperazine, and when m is 6 and cyclized, then (I) typically represents a substituted 2-keto-decahydroquinoxaline; $R_1$ and $R_4$ independently represent hydrogen, alkyl having from 1 to about 24 carbon atoms, hydroxyalkyl having from 1 to about 12 carbon atoms, haloalkyl having from 1 to about 12 carbon atoms, cyanoalkyl having from 2 to about 12 carbon atoms, aminoalkyl or iminoalkyl having from 1 to about 12 carbon atoms, ether groups having from 3 to about 18 carbon atoms, hydroxyalkyl ether or cyanoalkyl ether groups having from 4 to about 18 carbon atoms, alkenyl or aralkyl having from 7 to about 14 carbon atoms, alkylene having from 2 to about 7 carbon atoms and optionally containing a phosphite, ester or hindered phenol group; $R_4$ may be oxygen; and, $R_2$ and $R_3$ on the $N^4$-adjacent carbon of the fixed two-carbon bridge independently each represent alkyl having from 1 to about 12 carbon atoms, haloalkyl having from 1 to about 12 carbon atoms, cyanoalkyl having from 2 to about 12 carbon atoms, aminoalkyl or iminoalkyl having from 2 to about 12 carbon atoms, cycloalkyl having from 5 to about 14 carbon atoms, hydroxycycloalkyl having from 5 to about 14 carbon atoms, alkenyl and aralkyl having from 7 to about 14 carbon atoms, alkylene having from 2 to about 7 carbon atoms and optionally containing a phosphite, ester or hindered phenol group, and which in combination, one with another, represent cycloalkyl having from 5 to about 14 carbon atoms at least four of which are cyclized and optionally containing a keto, ester, amide, ether, thio or hydroxy group.

When it is desired to prepare a compound having a substituted alkylene group in the variable length bridge of the above-identified structural formula (I), the compound may be represented by a structural formula selected from

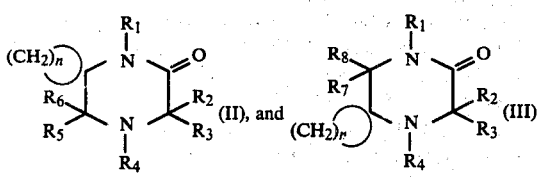

wherein n represents an integer in the range from 0 to about 6; so when n is 0 then (II) and (III) represent substituted 2-keto-piperazine, and when n is 4 with the variable length bridge cyclized, then (II) and (III) represent 2-keto-decahydroquinoxaline; and, $R_5$, $R_6$, $R_7$, $R_8$ in the variable length bridge have the same connotation as $R_2$ and $R_3$ in (I) hereinabove, and additionally may be H, except that $R_5$ and $R_6$ are different if either is H; $R_2$, $R_3$ may be cyclizable, as may be $R_5$, $R_6$, $R_7$, $R_8$; and, if cyclized, the cyclic substituents may be the same or different.

Illustrative of the type of substituents that provide effective stabilization in the above-identified 2-keto-diazacycloalkanes II and III are:

where $R_1$ and/or $R_4$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R_1$ and/or $R_4$ is hydroxyalkyl, examples are 2-hydroxyethyl, 2-hydroxypropyl, 3-hydroxypropyl, 2-hydroxybutyl, 6-hydroxyhexyl, 8-hydroxyoctyl, and the like;

where $R_1$ and/or $R_4$ is haloalkyl, examples are 2-chloroethyl, 2-bromoethyl, 2-fluoroethyl, 2-chlorobutyl, 4-chlorobutyl, 2-chloroethylhexyl, and the like;

where $R_1$ and/or $R_4$ is cyanoalkyl, examples are 2-cyanoethyl, 3-cyanopropyl, 4-cyanobutyl, 8-cyanooctyl, and the like;

where $R_1$ and $R_4$ is aminoalkyl or iminoalkyl, examples are 2-aminoethyl, 3-aminopropyl, 4-aminobutyl, 6-aminohexyl, 2-methyl-2-aminoethyl, and the like;

where $R_1$ and $R_4$ is ether, examples are methoxyethyl, ethoxyethyl, ethoxypropyl, octyloxyethyl, phenoxyethyl, p-methylphenoxypropyl, and the like; where $R_1$ and $R_4$ is hydroxyalkylether or cyanoalkyl ether, examples are 2-hydroxyethyloxaethyl, p-(2-hydroxypropyl)-phenyloxapropyl, 4-hydroxybutyloxahexyl, 2-cyanoethyloxaethyl, 2-hydroxyethyl-di(oxaethyl), and the like;

for $R_2$, $R_3$, $R_5$, $R_6$, $R_7$, and $R_8$, examples are methyl, ethyl, propyl, n-butyl, isobutyl, n-hexyl, 2-ethylheptyl, n-decyl, and where the substituents are cyclizable, cyclopentyl, methylcyclopentyl, cyclohexyl, methylcyclonexyl, dimethyl cycloheptyl, piperidyl, 2-2',6-6'-tetramethyl piperidyl, and the like.

Examples of specific substituted mono-keto-diazacycloalkan-2-ones derived from compounds prepared by the syntheses of this invention, wherein the $N^4$-adjacent C atom of the fixed two carbon bridge has two substituents which may be cyclizable, are:

(a) diazamonocycloalkan-2-ones having a total of more than four substituents on the diaza ring, for example, 3,3,5,5,6-pentaalkyl-1,4-piperazin-2-one;

(b) trans-1,4-diazabicycloalkan-2-ones for example, trans-3,3-dialkyl-decahydroquinoxalin-2-one; and (c) mono keto-diazatricycloalkan-2-ones, for example, 3,3-($\beta,\beta'$-ditert-butylamine)decahydroquinoxalin-2-one.

The more preferred substituted 2-keto-1,4-diazacycloalkane compounds are those wherein: $R_1$ and/or $R_4$ is selected from the group consisting of alkyl having from 4 to 18 carbon atoms, benzyl, cyclohexylmethyl, hydroxyalkyl having from 1 to about 6 carbon atoms, hydroxyalkyl ether having from 4 to about 12 carbon atoms, cyanoalkyl having from 2 to about 6 carbon atoms, and aminoalkyl having from 1 to about 6 carbon atoms, $R_2$, $R_3$, $R_5$, $R_6$, $R_7$ and $R_8$ are selected from the group consisting of alkyl having from 1 to about 12 carbon atoms, and polymethylene having from 5 to 6 carbon atoms which are cyclizable; only $R_2$, $R_3$ may be cyclized, or $R_2$, $R_3$ and $R_5$, $R_6$ may be cyclized; and if $R_2$, $R_3$, and $R_5$, $R_6$ are each cyclized; the cyclic substituents are different; and n is a numeral in the range from 4 to about 6 when the methylene groups are cyclized.

Examples of the aforespecified more preferred substituted mono-keto-diazaalkan-2-ones are:

$N^4$-($\beta$-hydroxyethyl)-3,3,6-trimethyl-piperazin-2-one;
$N^4$-($\beta$-hydroxyethyl)3,3-pentamethylene-5,5-dimethyl-piperazin-2-one;
$N^4$-($\beta$-hydroxyethyl)3,3,6-trimethyl-diazepin-2-one;
$N^4$-($\beta$-hydroxyethyl)3,3,6,6-tetramethyl-diazepin-2-one;
$N^4$-($\beta$-hydroxyethyl)3,3-pentamethylene-5,5-hexamethylene-diazepin-2-one;
$N^4$-($\beta$-hydroxyethyl)3,3-pentamethylene-diazepin-2-one;
$N^4$-($\beta$-hydroxyethyl)3,3,5,5,7,7-hexamethyl-diazepin-2-one;
$N^4$-($\beta$-hydroxyethyl)3,3-pentamethylene-5,5,7,7-tetramethyl-diazepin-2-one;
$N^4$-($\beta$-hydroxyethyl)3,3-dimethyl-5,5-pentamethylene-piperazin-2-one;
$N^4$-($\beta$-hydroxyethyl)3,3,6,6-tetraethyl-5,5-pentamethylene-diazepin-2-one;
$N^4$-($\beta$-hydroxyethyl)3,3-dimethyl-5,6-tetramethylene-diazeine-2-one;
$N^4$-($\beta$-hydroxyethyl)3,3,5,5-tetramethyl-6,7-tetramethylene-diazepin-2-one;
cis-3,3-dimethyl-decahydroquinoxalin-2-one;
cis-3,3-pentamethylene-decahydroquinoxalin-2-one;
cis-$N^1$-(3',5'-di-t-butyl-4-hydroxybenzyl)3,3-dimethyl-decahydroquinoxalin-2-one);
trans-$N^1$-(3',5'-di-t-butyl-4-hydroxybenzyl)3,3-dimethyl-decahydroquinoxalin-2-one;
1,4-butane-bis[$N^1$-(3,3-dimethyl-decahydroquinoxalin-2-one)];
trans-1,6-hexanediol-bis[$N^1$-(3,3-dimethyl-decahydroquinoxaline-2-one)di-carboxylate];
trans-1,6-hexan-bis[$N^1$-(3,3-pentamethylene-decahydroquinoxalin-2-one)di-carboxylate]; and, trans-$N^1$-carbobutoxy-3,3-dimethyl-decahydroquinoxalin-2-one.

Most preferred substituted mono-keto-1,4-diazaalkan-2-ones are:

$N^1$-dodecyl-3,3,5,5-tetramethyl-2-piperazinone;
$N^1$-t-octyl-3,3,5,5-tetramethyl-2-piperazinone;
1,2-ethane-bis-($N'$-3,3,5,5-tetramethyl-2-piperazinone;
$N^4$-t-octyl-3,3,6-tetramethyl-2-piperazinone;
$N^1$-phenyl-3,3,5,5-tetramethyl-2-piperazinone;
$N^1$-butyl-3,3-dimethyl-5,5-pentamethylene-2-piperazinone;
$N^1$-butyl-3,3,5,5,7-pentamethyl-1,4-diazepin-2-one;
trans-3,3-pentamethylenedecahydroquinoxalin-2-one;
trans-3,3-dimethyl-decahydroquinoxalin-2-one;
trans-3,3-dimethyl-$N^4$-$\beta$-hydroxyethyl-decahydroquinoxalin-2-one;
trans $N^1$-dodecyl-3,3-dimethyl-decahydroquinoxalin-2-one;

trans-N¹-benzyl-3,3-dimethyl-decahydroquinoxalin-2-one;

trans-N¹-dodecyl-3,3-pentamethylene-decahydroquinoxalin-2-one;

trans N¹-3,3-pentamethylene-decahydroquinoxalin-2-one;

trans-3,3-dimethyl-N⁴-β-hydroxyethyl-decahydroquinoxalin-2-one.

It will now be evident that many of the substituents identified hereinabove may not be made directly by the syntheses of this invention, but by additional steps after having formed the substituted 2-keto-1,4-diazacycloalkane. These additional steps are well known to those skilled in the art, and do not require detailed description herein. In particular, dimers and bis compounds of substituted 2-keto-1,4-diazacycloalkanes can be prepared by known methods, once the desired 2-keto-1,4-diazacycloalkane is obtained by a chosen synthesis.

A. Hydrogenation of Unsaturated 2-keto Precursor (Synthesis "A"):

Hydrogenation of 3,4-dihydroquinoxalin-2-one with substituents, which may be cyclizable, on the N⁴-adjacent C atom of the fixed two-carbon bridge, yields the decahydroquinoxalin-2-one. For example, hydrogenation may be effected with Adams catalyst, ruthenium, rhodium, Raney nickel, or other suitable hydrogenation catalyst, at a temperature in the range from about 100° C. to about 300° C. and a pressure in the range from about 1000 psi to about 3000 psi, to yield 3,3-dialkyl-decahydroquinoxalin-2-one. The product so obtained may thereafter be further reacted with preselected reactants to provide desired substituents on the N¹ atom, the N⁴ atom or both in a known manner. Bis compounds and dimers may be prepared.

In another particular embodiment, 3,3-pentamethylene-3,4-dihydroquinoxalin-2-one may be hydrogenated with a hydrogenation catalyst to yield 3,3-pentamethylene-1,4-decahydroquinoxalin-2-one. Further substituents on the N¹ and N⁴ atoms may be made by conventional means, some of which are more fully described in concurrently filed and copending U.S. patent application Ser. No. 835,065 which is incorporated herein by reference as if fully set forth.

B. Reaction of Trans-1,2-diaminocycloalkane with Cyanohydrin in Aqueous Medium (Synthesis "B"):

As stated hereinbefore, the Bindler reference U.S. Pat. No. 2,920,077 taught that cis-1,2-diaminocyclohexane reacts with acetone cyanohydrin to give cis-3,3-dimethyl-decahydroquinoxalin-2-one (also identified as 3,3-dimethyl-5,6-tetramethylene-2-ketopiperazine) which melts at 165°–166° C., but that trans-1,2-diaminocyclohexane behaves differently. Nevertheless it has now been found that trans-1,2-diaminocyclohexane reacts with various α-hydroxy fatty acid nitriles, and are cyclized to yield a 1,4-diazacycloalkane reaction product. Generally useful are the cyanohydrins of aliphatic, araliphatic or cycloaliphatic carbonyl compounds which cyclize forming a fixed two-carbon bridge between the N¹ and N⁴ atoms of the diaza ring. Preferred are formaldehyde cyanohydrin, acetaldehyde cyanohydrin, hydrocinnamaldehyde cyanohydrin, acetone cyanohydrin, methyl ethyl ketone cyanohydrin, cyclohexanone cyanohydrin and the like.

The reaction is carried out by adding a preselected cyanohydrin at room temperature dropwise into a solution of trans-1,2-diaminocyclohexaine in water. The mixture is stirred and gradually heated to a temperature in the range from about 80° C. to about 100° C. at ambient pressure, until the reaction is completed. The product is recovered by removing the aqueous phase. The product may be solid, semisolid, or liquid, is generally insoluble in the aqueous phase, and is usually visible as a separate organic phase.

C. The Cyanohydrin Reaction (Synthesis "C"):

It has been found that 1,2-diamines may be reacted with a cyanohydrin in an organic solvent for the reactants, in the presence of aqueous alkali, provided there is also supplied an "onium salt" catalyst and a haloform. By "onium salts" I refer to ternary or quaternary salts such as are generally used in the phase transfer catalysis of heterogeneous reactions in immiscible liquids. The necessary requirement for the onium salt chosen is that it be soluble in both liquid phases, and usually a little more soluble in the organic phase than the aqueous phase. A wide variety of onium salts is effective in this ketoform synthesis. These onium salts include the well-known salts of Group VA of the Periodic Table, and some Group VIA elements such as are disclosed in a review in Angewandte Chemie, International Edition in English, 16 493–558 (August 1977). Discussed therein are various anion transfer reactions where the onium salt exchanges its original ion for other ions in the aqueous phase, making it possible to carry out chemistry there with the transported anion, including OH⁻ ions.

The onium salts used in this synthesis include one or more groups having the formula $(R_nY)^+X^-$, wherein Y is either a pentavalent ion derived from an element of Group VA, or a tetravalent ion derived from an element of Group VIA; R is an organic moiety of the salt molecule bonded to Y by four covalent linkages when Y is pentavalent, and three covalent linkages when Y is tetravalent; $X^-$ is an anion which will dissociate from the cation $(R_nY)^+$ in an aqueous environment. The group $(R_nY)^+X^-$ may be repeated as in the case of dibasic quaternary salts having two pentavalent Group VA ions substituted in the manner described.

The preferred onium salts for use in the invention have the formula

$(R^1R^2R^3R^4Y^+)X^-$ wherein Y is N or P, and $R^1$–$R^4$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The onium salts are generally selected to be less preferentially less soluble in the less polar of the two distinct liquid phases. Any of the salts disclosed in U.S. Pat. No. 3,992,432 will be found effective, but most preferred are those in which the total number of carbon atoms in $R^1, R^2, R^3$, and $R^4$ cumulatively range from about 13 to about 57, and preferably range from about 16 to about 30. Most preferred onium salts have Y=N, and hydrocarbon radicals where $R^1$ is $Ch_3$, and $R^2$, $R^3$, and $R^4$ are each selected from the group consisting of n-C₄H₅; n-C₅H₁₁; mixed C₅H₁₁; n-C₆H₁₃; mixed C₆H₁₃; C₆H₅; C₆H₅CH₂; n-C₈H₁₇; n-C₁₂H₂₅; n-C₁₈H₃₇; mixed C₈–C₁₀ alkyl; and the like. However, $R^1$ may also be selected from C₂H₅, n-C₃H₇ and n-C₄H₉.

Various counterions may be used, including Cl⁻, Br⁻, I⁻, NO₃⁻, SO₄⁼, HSO₄⁻ and CH₂CO₂⁻. Most preferred is Cl⁻.

The cyanohydrin reaction may be carried out at any temperature within a wide range from about the freezing point of the reaction mass to about the reflux temperature of the solvent, provided the reaction temperature is below that deleterious to the 2-keto-1,4-diazacycloalkane formed. The reaction is of particular interest because it generally proceeds at room temperature at satisfactory speed, in about 4 to 5 hours, which is substantially faster than the synthesis "B" cyclization, and with better yields. The reaction may also be carried out at any desired pressure from subatmospheric to superatmospheric, but atmospheric pressure is preferably employed for convenience, and because there appears to be no substantial advantage to be gained from operating at higher pressures.

The 1,2-diamines may include two primary amine moieties, one primary amine moiety and one secondary amine moiety, or two secondary amine moieties. The amine is chosen to provide, upon cyclization, the desired number of C atoms in the variable length bridge, and also to provide the desired substituents on preselected C atoms of this bridge. It will thus be evident that a straight chain or acyclic diamine will be appropriate where a monocyclo-1,4-diazacycloalkane is to be synthesized.

The cyanohydrin chosen may be a cycloalkanone cyanohydrin, dialkyl ketone cyanohydrin, araalkyl ketone cyanohydrin or aldehyde cyanohydrin.

The organic solvent may be any solvent in which the reactants are soluble and include hydrohalomethylenes, particularly hydrochloromethylenes, sulfolane, dibutyl ether, dimethyl sulfone, diisopropyl ether, di-n-propyl ether, 1,4-dioxane, tetrahydrofuran, benzene, toluene, hexane, carbon tetrachloride and the like. Most preferred solvents are hydrochloromethylenes.

The preferred aqueous alkali is an alkali metal hydroxide solution such as concentrated aqueous sodium hydroxide, or potassium hydroxide, preferably in the range from about 20 percent to about 70 percent. The amount used is not critical but at least a trace amount appears to be essential for the progress of the desired reaction. It is most preferred to use sufficient aqueous alkali solution to form a visually distinct aqueous phase in the presence of the organic solvent phase, and it is preferred that at least 5 percent by weight of the reaction mass be aqueous alkali solution. There is no advantage to using an amount more than about 75 percent by weight of the reaction mass. In general, a solid reaction product is formed as a result of the reaction.

The presence of a haloform, such as chloroform, iodoform or bromoform appears to take part in the reaction, presumably as a catalyst, though the precise mechanism or the manner in which the haloform affects the reaction, is not understod. This hypothesis that a haloform is essential is based upon the fact that, when another solvent is substituted for the haloform, the reaction does not proceed without at least a trace of the haloform. The amount of haloform used does not appear to be critical, and only a minor amount by volume, as compared with the volume of organic solvent used, suffices. A preferred amount of haloform is in excess of 20 percent by weight of the reaction mass, and chloroform is most preferred.

Though the amount of onium salt catalyst used is not critical, its catalytic function appears to be unique in this cyanohydrin reaction. In general, it is sufficient to use no more onium salt catalyst than about 2 percent by weight of the reaction mass, and it is preferred to use in the range from about 0.1 to about 1 percent by weight.

D. The Ketoform Synthesis (Synthesis "D")

It has been found that 1,2-diamines may be reacted with a saturated or unsaturated monoketone or monoaldehyde and a haloform reactant, in an organic solvent for the reactants, in the presence of aqueous alkali, provided there is also supplied an onium salt catalyst such as described hereinabove in Synthesis C. The reaction may be carried out at any temperature within a wide range from about the freezing point of the reaction mass to about the reflux temperature of the solvent, provided it is lower than a temperature which is deleterious to the 2-keto-1,4-diazacycloalkane formed. The reaction is of particular interest because it generally proceeds at room temperature at satisfactory speed, substantially faster than the aforedescribed synthesis "B," with better yields. The reaction may also be carried out at any desired pressure from subatmospheric to superatmospheric, but atmospheric pressure is preferably employed for convenience, and because there appears to be no substantial advantage to be gained from operating at higher pressures.

The same 1,2-diamines are used which were used hereinbefore, and as before, may be chosen to provide upon cyclization, the desired number of C atoms in the variable length bridge, and also to provide the desired substituents on preselected C atoms of this bridge. Also as before, a cyclic diamine will be appropriate where a bicyclo-1,4-diazacycloalkane is to be synthesized.

The mono-ketone is preferably saturated and may be cyclic or acyclic. Useful ketones are those which cyclize forming a fixed two-carbon bridge between the $N^1$ and $N^4$ aoms of the diaza ring. Preferred monoketones are cycloalkanones, dialkylketones and aralkylketones.

The monoaldehyde is preferably saturated and may be cyclic or acyclic. Useful monoaldehydes are those which cyclize forming a fixed two-carbon bridge between the $N^1$ and $N^4$ atoms of the diaza ring. Preferred monoaldehydes are cycloaldehydes, dialkylaldehydes and aralkylaldehydes.

It will presently be recognized from the examples herein, that polyketones and polyaldehydes, for example diketones and dialdehydes, will yield bis compounds.

The presence of haloform in the reaction mass is essential, and it appears that the haloform is a reactant while the onium salt provides the catalytic action. Preferred haloforms are chloroform and bromoform. It is essential that at least a stoichiometric amount of haloform be used if no amine is to be left unreacted. Though a small amount of unreacted amine is not deleterious, it is desirable to employ a slight excess over stoichiometric of the haloform. Though an excess up to about a 50% excess over stoichiometric provides acceptable results, more than 50% over stoichiometric is to be avoided because of the formation of undesirable side products.

The preferred aqueous alkali is an alkali metal hydroxide solution such as aqueous sodium hydroxide, or potassium hydrozide, preferably in the range from about 20 percent to about 70 percent. The amount used is not critical but at least a trace amount appears to be essential for the progress of the desired reaction. It is preferred to use sufficient aqueous alkali solution to form a visually distinct aqueous phase in the presence of the organic solvent phase. In general, the amount of aqueous alkali used is preferably at least 5 percent by weight of the reaction mass. There is no advantage to using more aqueous alkali than about 75 percent by weight of the reaction mass.

Though the amount of onium salt catalyst used is not critical, its catalytic function appears to be unique in this ketoform synthesis. In general, it is sufficient to use less than 2 percent by weight of the reaction mass, and it is preferred to use in the range from about 0.1 to about 1 percent by weight.

In general, this synthesis "D" described immediately hereinabove, will provide a 2-keto-1,4-diazacycloalkane with substituents both at the 5-position (that is, the $N^4$-adjacent C atom of the variable length bridge), and also the $N^1$-adjacent C atom of the variable length bridge. In addition, where an amine moiety has an alkyl (say) substituent either the $N^1$ or $N^4$ atom, or both, may be alkyl substituted. Thus, starting with N-propyl-2-methyl-1,2-proppanediamine, the synthesis yields both $N^1$-propyl-3,3,5,5-tetramethyl-2-piperazinone and $N^4$-propyl-3,3,6,6-tetramethyl-2-piperazinone.

The following examples serve to illustrate the invention. Where not otherwise stated, parts are given as parts by weight and the temperatures in degrees centigrade.

EXAMPLE 1

Preparation of 3-hexyl-3-methyl-cis-decahydroquinoxalin-2-one by synthesis "A":

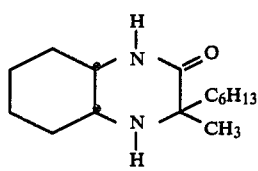

1.5 g 3-hexyl-3-methyl-3,4-dihydroquinoxalin-2-one in 30 ml ethanol is hydrogenated at about 180° C. and under about 2000 psi in the presence of 0.4 g ruthenium (5%) on charcoal. Hydrogenation is allowed to proceed for about 3 hours after which the hydrogenated mixture is filtered. The solvent is then removed and the residue distilled under 0.2 mm Hg at about 157°–158° C., to yield about 1.1 g of an oily product which upon trituration with hexanes, gives a white solid. The above structure is confirmed by IR, NMR, GC and mass spectrometer data.

In a manner analogous with the foregoing, 3,3-dimethyl-3,4-dihydroquinoxalin-2-one is hydrogenated at about 130° C. and 1500 psi in the presence of rhodium (5%) on charcoal in 2 hours, to yield cis-3,3-dimethyl-decahydroquinoxalin-2-one.

Other cis-2-keto-1,4-diazacycloalkane compounds which are polysubstituted polycyclic compounds may be formed by contacting a precursor polysubstituted polycyclic unsaturated 2-keto-1,4-diaza compound with hydrogen in the presence of a hydrogenation catalyst at a temperature above about 100° C. but below a temperature which is deleterious to the polycyclic cis-2-keto-1,4-diazacycloalkane formed. Polysubstituted polycyclic trans-2-keto-1,4-diaza unsaturated compounds are not similarly obtained by hydrogenation.

EXAMPLE 2

A. Preparation of trans-3,3-dimethyl-1,4-decahydroquinoxalin-2-one by synthesis "B":

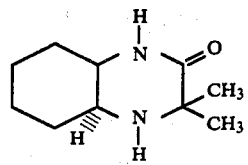

A mixture of cis and trans isomers of 1,2-diaminocyclohexane are dissolved in 500 ml water in a 3-necked flask, and acetone cyanohydrin was slowly added over a period of 45 mins. The mixture was stirred for an additional hour at room temperature, then warmed to 90°–95° C. and maintained at that temperature for 20 hrs. The reaction mixture was then cooled, filtered and the water removed from the filtrate. Crystals obtained by recrystallization from acetone were found to be the trans isomer of 3,3-dimethyl-decahydroquinoxalin-2-one. The melting point of the crystals was about 218.5°–219.5° C.

Elemental analysis calculated: 65.9%C; 15.37%N; 9.95%H. Analysis found: 66.23%C; 15.53%N; 20.06%H.

B. In a manner analogous to that described hereinbefore in Example 2A, replacing acetone cyanohydrin whith cyclohexanone cyanohydrin, gives trans-3,3-pentamethylene-decahydro-2-quinoxalinone, a compound also obtained by synthesis "D," as examplidfied hereinafter in Example 11.

EXAMPLE 3

Symmetrical $N^4$-adjacent C atoms may each be disubstituted, and primary, secondary and tertiary alkyl substituents may be had on the $N^1$ atom of the diaza ring by the cyanohydrin synthesis.

Preparation of $N^1$-propyl-3,3,5,5-tetramethyl-2-piperazinone by the cyanohydrin reaction, synthesis "C": (one primary and one secondary amine moieties)

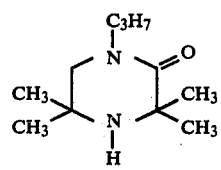

6.5 g of $N^1$-propyl-2-methyl-1,2-propanediamine was dissolved in 50 ml chloroform in a 250 ml flask cooled in an ice-bath. Bromoform may also be used. 20 ml concentrated NaOH (50% by weight) was added followed by 0.5 g benzyltriethylammonium chloride (hereafter "BTAC"). 5.5 g acetone cyanohydrin was then added dropwise in 3 min. The ice was allowed to melt and the bath warmed slowly to room temperature. After about 5.5 hr the reaction mixture is filtered and washed thoroughly with chloroform. The combined chloroform solution was washed several times with 50 ml water, dried with sodium sulfate and concentrated. The oil was distilled at 117°–121° C. under 10 mm Hg to collect 4.6 g of a colorless oil. The structure of the compound is supported by IR, GC, NMR and mass spectrometer data.

In a manner analogous to that described immediately hereinabove, $N^1$-isopropyl-3,3,5,5-tetramethyl-2-piperazinone is prepared from $N^1$-isopropyl-2-methyl-1,2-propanediamine, and $N^1$-t-octyl-3,3,5,5-tetramethyl- 2-piperazinone is prepared from N¹-t-octyl-2-methyl-1,2-propane diamine.

EXAMPLE 4

Preparation of N¹-t-butyl-3,3,5,5-tetramethyl-2-piperazinone by cyanohydrin reaction, synthesis "C," with the order of addition of reactants changed:

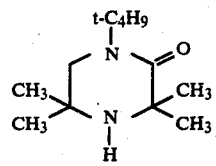

7.2 g of N¹-t-butyl-2-methyl-1,2-propane diamine was dissolved in 14.4 g chloroform in a 250 ml flask cooled in an ice-bath. 5.5 g acetone cyanohydrin was added, and then 80 g conc NaOH (50% by weight) is dripped in slowly over a period of about 3 min. keeping the temperature below 10° C. The ice was allowed to melt and the reaction mixture warmed slowly to room temperature. After about 3 hr the mixture was worked up in a manner analogous to that described hereinabove. The reaction product solidifies upon standing. It is recrystallized from pentane to yield 6.5 g of colorless crystals, melting point 104°–105° C. The foregoing structure of the compound is supported by GC, NMR, IR and mass spectrometer data.

In an analogous manner, preselected acyclic alkyl 1,2-diamines may be used to provide the desired substituents on carbon atoms of the variable length bridge; similarly, aralkyl-1,2-diamines and cycloalkyl-1,2-diamines may be used to prepare bicyclo-1,4-diazacycloalkanes.

EXAMPLE 5

A. Preparation of N¹-isopropyl-3,3,5,5-tetramethyl-2-piperazinone with bromoform by the cyanohydrin reaction synthesis "C":

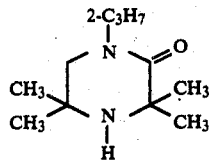

In a 250 ml 3-necked flask equipped with an air stirrer, thermometer, and dropping funnel, place 13.02 g N'-isopropyl-2-methyl-1,2-propanediamine, 53.08 g bromoform, 9.36 g acetone cyanohydrin, and 0.45 g BTAC. The mixture is cooled in an ice-bath to keep the reaction temperature below 10° C., and 128 g NaOH (50% by wt) was added dropwise over about 2 hrs. The reaction is highly exothermic, the temperature rising to 12° C. once, and to 10° C. several times. The mixture was allowed to stir in the ice-bath for about 3 hrs, dissolved in a minimal amount of water, and then enough dichloromethane was added to provide two distinct layers. The aqueous layer is extracted twice with 50 ml dichloromethane, washed and worked up in the usual manner. The product solidified after removing bromoform under vacuum. Recrystallization from pentane yields 9.1 g pure crystals, melting point 81°–82° C.

B. In a manner analogous to that described in Example 5A hereinabove, starting with N¹-(1-hydroxy-2-methyl-2-propyl)-2-methyl-1,2-propanediamine, acetone cyanohydrin and chloroform which are reacted in the presence of an onium salt in aqueous alkaline solution, a compound identified as 1-(1-hydroxy-2-methyl-2-propyl)-3,3,5,5-tetramethyl-piperazin-2-one is obtained having the structure

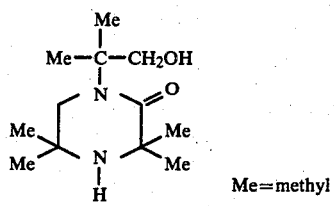

After the reaction, the reaction product is worked up in a manner analogous to that described hereinbefore, and upon recrystallization from hexane, colorless crystals are obtained having a melting point of 85° C.

C. In a manner analogous to that described in Example 5A hereinabove, starting with N¹,N³-di-tert-butyl-2-methyl-1,2,3-propanetriamine, acetone and chloroform, and also adding an onium salt in aqueous alkali solution, a reaction occurs which yields a compound identified as 1-tert-butyl-3,3,5-trimethyl-5-(N-tert-butyl-aminomethyl)-piperazin-2-one, having the structure

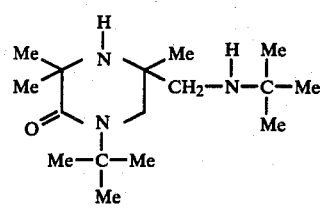

The reaction product is worked up as before, and the product obtained is recrystallized from pentane to yield colorless crystals having a melting point of 53°–55° C.

D. In a manner analogous to that described in Example 5A hereinabove, starting with N¹-phenyl-2-methyl-1,2-propanediamine, acetone cyanohydrin, and chloroform, and carrying out a reaction in a manner analogous to that stated therein, a compound is obtained which is identified as 1-phenyl-3,3,5,5-tetramethyl-piperazin-2-one, having the structure

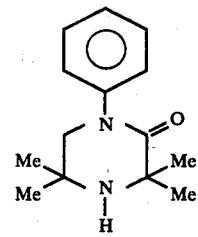

Upon workup in a manner analogous to that described hereinabove, and recrystallization of the product from hexane, colorless crystals are obtained having a melting point of 93°–95° C.

EXAMPLE 6

Preparation of N¹-(butyl)-3,3,5,5,7-pentamethyl-1,4-diazepin-2-one, by cyanohydrin synthesis "C":

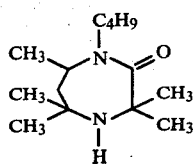

N$^1$-butyl-4-methyl-2,4-pentanediamine and acetone cyanohydrin are reacted in the presence of conc NaOH (50% by wt) and a quaternary ammonium chloride catalyst such as BTAC in a chloroform medium. The reaction is commenced in an ice-cold flask while the chloroform is slowly dripped into it. The reaction is allowed to proceed at ice-bath temp for about 2 hr, then warmed to room temp and maintained for another couple of hours. The reaction product is worked up, filtered and washed with CHCl$_3$ several times to yield the above-identified product. The structure is supported by IR, NMR, GC and mass spectrometer data.

In an analogous manner other alkyl diamines and cyclic 1,2-diamines such as o-phenylenediamine and cyclohexyldiamine may be used, and other alkyl cyanohydrins having a carbonyl moiety, and cyclic cyanohydrins such as cycloalkanone cyanohydrins may be used.

EXAMPLE 7

Preparation of N$^1$,N$^4$-dimethyl-3,3-dimethyl-2-piperazinone by ketoform synthesis "D":

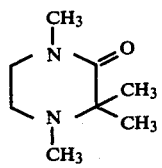

8.8 g N,N'-dimethyl-ethylene diamine, 12.0 g CHCl$_3$, and 6.0 g acetone are placed in a 250 ml flask in an ice-bath, and 1.1 g BTAC added. To provide a homogeneous organic liquid phase, 100 ml dichloromethane is added. Then 40 ml conc NaOH (50% by wt) is dripped into the flask over about 30 mins. The reaction is allowed to proceed for about 5 hr and the reaction product is worked up as described in Example 5 hereinabove. Upon distillation the product is obtained. The foregoing structure of the compound is supported by IR, NMR, GC and mass spectrometer data.

EXAMPLE 8

In a manner analogous to that described in Example 7 hereinabove, N$^1$-propyl-3,3,5,5-tetramethyl-2-piperazinone is prepared according to Synthesis "D," utilizing acetone, chloroform, and a phosphonium salt. The specific phosphonium salt used is (C$_4$H$_9$)$_3$P$^+$C$_{16}$H$_{33}$Br$^-$. Upon working up in the usual manner, pure white crystalline needles of product are obtained.

EXAMPLE 9

Preparation of N$^1$-propyl-3,3,5,5-tetramethyl-2-piperazinone (I) and N$^4$-propyl-3,3,6,6-tetramethyl-2-piperazinone (II) by ketoform synthesis "D": (one primary and one secondary amine moieties)

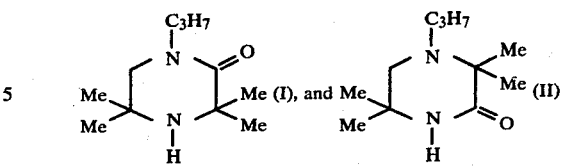

6.5 g N-propyl-2-methyl-1,2-propanediamine and 50 ml methylene chloride are placed in a 250 ml flask. 32 g acetone and 6.9 g chloroform are added to the flask, followed by 0.5 g BTAC. While stirring in an ice-bath, 20 ml conc NaOH (50% by wt) was added dropwise over about 0.5 hr. Water is added after 6.5 hr until all solids go into solution. Two distinct liquid phases are formed, and the layers are separated. The aqueous layer is extracted several times with 40 ml methyl chloride. The combined methylene chloride solutions are washed several times with H$_2$O, dried and concentrated. 8.6 g of a light yellow oil are obtained which is identified as (I) and (II) in a 7:3 ratio. The oil is distilled at 125°–7° C./8 mm and a colorless oil mixture of the compounds (I) and (II) is obtained. The foregoing structure of the compounds is supported by IR, NMR, GC and mass spectrometer data.

EXAMPLE 10

Preparation of 3,3-pentamethylene-2-quinoxalinone by ketoform synthesis "D": (two primary amine moieties)

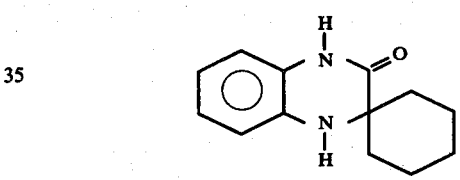

In a 500 ml 3-neck flask place 10.8 g of o-phenylene diamine in 120 ml dichloromethane. Add 14.7 g of cyclohexanone and 18.06 g of chloroform, and stir. While stirring, 1.14 g of BTEA are added to the flask. Then add 40 ml conc NaOH (50% by wt) to the reaction mixture dropwise, so the temperature does not exceed 30° C. The reaction mixture is stirred overnight. Two distinct phases are formed which are separated, filtered, and worked up to yield 20 g off-white solid after washing with H$_2$O (insoluble in both aqueous base and CH$_2$Cl$_2$). The CH$_2$Cl$_2$ solution is concentrated after drying. Cyclohexanone is distilled off under vacuum, and the residue triturated with benzene to obtain 1 g more of solid. The total yield is 11 g (51% by wt). The solid is dissolved in ethanol and conventionally hydrogenated.

Hydrogenation is conveniently effected with metal catalysts such as reduced nickel, Raney nickel, rhodium, ruthenium, platinum oxide or palladium, preferably deposited on a support such as charcoal. The temperature of reaction is from about 20° C. to about 350° C. Times of reaction are from about 0.5 to 8 hours or more. High pressures, ranging up to 2000 psig are characteristic of the process. The hydrogenated compound is identified by carbon, hydrogen, nitrogen analysis, mass spectrometry and NMR spectroscopy, as cis-decahydro-3,3-pentamethylenequinoxalin-2-one. (A Perkin-Elmer Model 270 or duPont Model 21-490 mass spectrometer and a Varian A-60 NMR spectrometer are used).

B. In a manner analogous to that described in Example 10A hereinabove, BTAC is replaced with 1.5 g Aliquat* 336, stated to be N-methyl-N,N,N-tri(octyl,decyl) ammonium chloride. The product obtained is the same as that obtained with BTAC.

When 0.5 parts of the novel hydrogenated compound formed in each of the foregoing examples 10A and 10B is blended into 100 parts polypropylene, and the composition is formed into film and tested in a manner analogous to that described in Example 1, the tests indicate that the composition is UV stable fore more than 6000 hrs.

EXAMPLE 11

Preparation of trans-3,3-pentamethylene-decahydro-2-quinoxalinone by ketoform synthesis "D":

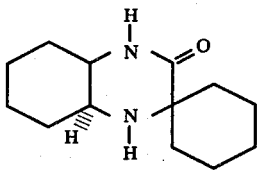

In a 500 ml flask is placed 5.7 g of trans-1,2-diaminocyclohexane and 100 ml dichloromethane. 5.9 g cyclohexanone and 6.6 g chloroform are added, followed by 0.57 g BTAC. While stirring, 25 ml conc NaOH (50% by wt) are added very slowly in about 30 min. The reaction mixture is stirred overnight, then refluxed for 5 hr. As in the foregoing example, two layers of liquid are formed, and the reaction mixture is worked up and triturated with acetone. About 0.5 g of white solid is obtained. The above structure of the compound is supported by IR, NMR, GC and mass spectrometer data.

In an analogous manner, a mixture of cis- and trans- isomers of 1,2-diamino-cyclohexane is reacted with cyclohexanone and chloroform to yield a mixture of cis- and trans-isomers of 3,3-pentamethylene-decahydro-2-quinoxalinone.

EXAMPLE 12

Preparation of 3-hexyl-3-methyl-cis-decahydroquinoxalin-2-one by the ketoform synthesis "D": (two primary amine moieties). This compound was made in Example 1 by synthesis "A"

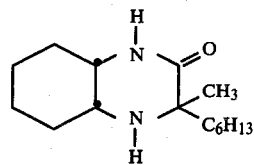

5.4 g o-phenylenediamine and 70 ml CHCl3 are placed in a 250 ml flask cooled in an ice-bath. 10.2 of 2-octanone are added followed by 0.5 g BTAC. While stirring, 25 ml conc NaOH (50% by wt) are added dropwise in 30 min. The reaction mixture is kept in an ice-bath for 2.5 hrs, then at room temperature overnight. Gas chromatography (F & M Scientific Corp. Model 810 using a 6'×0.25" column packed with 10% OV-17 silicone rubber (methyl and phenyl) is used) indicated absence of starting material. Water is added to dissolve the solid and the solution is separated into two layers. The aqueous layer is extracted with 40 ml CHCl3 and the combined CHCl3 solutions washed with water. The organic phase is dried and concentrated. An orange solid, identified as 3-hexyl-3-methyl-tetrahydroquinoxalin-2-one, is recovered, 1.5 g of which is dissolved in 30 ml ethanol and hydrogenated with 0.4 g ruthenium (5%) on charcoal at 180° C. under 2000 psi for 3 hrs. The product is filtered and the solvent removed. Upon distillation an oil is recovered which is triturated with hexanes to give a white solid. Upon recrystallization a white solid is recovered which melts at 115.7° C. and is identified as 3-hexyl-3-methyl-cis-decahydroquinoxalin-2-one.

0.5 parts of the novel hydrogenated compound is blended into polypropylene, and the composition is formed into film and tested in a manner analogous to that described in Example 1. The tests indicate that the composition is UV stable for more than 6000 hrs.

I claim:

1. A method for preparing a polysubstituted 2-keto-1,4-diazacycloalkane compound comprising reacting a diamine selected from the group consisting of an acyclic 1,2-diamine and a cyclic 1,2-diamine with a cyanohydrin selected from the group consisting of an acyclic cyanohydrin and a cyclic cyanohydrin, in the presence of (i) aqueous alkali (ii) an onium salt selected from the group consisting of the ternary salts of Group VIA elements and the quaternary salts of Group VA elements, and, (iii) a haloform selected from the group consisting of bromoform and chloroform; forming said polysubstituted 2-keto-1,4-diazacycloalkane compound; and, recovering said compound.

2. The method of claim 1 including adding a sufficient quantity of said aqueous alkali to form distinct organic and liquid phases.

3. The method of claim 2 wherein said acyclic 1,2-diamine is an alkyl diamine and said cyclic 1,2-diamine is selected from the group consisting of o-phenylene diamine and cyclohexyldiamine; said cyclic cyanohydrin is a cycloalkanone cyanohydrin and said acyclic cyanohydrin is an alkyl cyanohydrin derived from a ketone.

* * * * *